United States Patent [19]

Sih

[11] Patent Number: 4,931,399
[45] Date of Patent: Jun. 5, 1990

[54] PROCESS FOR PREPARING OPTICALLY-ACTIVE GLYCEROL KETAL DERIVATIVES

[75] Inventor: Charles J. Sih, Madison, Wis.

[73] Assignee: The Wisconsin Alumni Research Foundation, Madison, Wis.

[21] Appl. No.: 773,493

[22] Filed: Sep. 9, 1985

[51] Int. Cl.$^5$ .................... C07P 41/00; C12P 17/04
[52] U.S. Cl. .................... 435/280; 435/117; 435/135; 435/155; 435/156; 435/157; 435/126; 435/174; 435/176; 435/177; 435/253.5; 435/859; 435/886
[58] Field of Search ............ 435/117, 126, 135, 155, 435/156, 157, 280, 886, 859, 253, 253.5

[56] References Cited
PUBLICATIONS

Tanaka et al, *Agric. Biol. Chem.*, 44(1), 199–202 (1980).
Tanaka et al, *Agric. Biol. Chem.*, 48(8), 2135–2136 (1984).
Morgenlie, *Carbohydrate Research,* 107 (1982), 137–141.
Tsuda et al, *Chem. Pharm. Bull.*, 29(12), 3593–3600 (1981).
Fujita et al, *Tetrahedron Letters,* 23(34), 3507–3510 (1982).
Nelson et al, *J. Org. Chem.*, 42(6), 1006–1012 (1977).
Baer et al, *J.A.C.S.*, 61(4), 761–5 (1939).
Jung et al, *J.A.C.S.*, 102, 6304–11 (1980).
Baer, *Biochem. Prep.*, 2, 31–39 (1952).

*Primary Examiner*—Charles F. Warren
*Assistant Examiner*—Carolyn S. Elmore
*Attorney, Agent, or Firm*—Andrus, Sceales, Starke & Sawall

[57] ABSTRACT

The invention relates to a method for microbiologically resolving racemic 2,3-o-substituted glycerol esters to obtain optically activated 2,3-o-substituted glycerol with remaining esters also being optically active.

11 Claims, No Drawings

PROCESS FOR PREPARING OPTICALLY-ACTIVE GLYCEROL KETAL DERIVATIVES

TECHNICAL FIELD

This invention relates to the preparation of chiral glycerol ketals.

More specifically, this invention relates to the kinetic resolution of racemic 2,3-o-substituted glycerol esters.

Still more specifically, this invention relates to the kinetic resolution of racemic 2,3-o-substituted glycerol esters by microbiological means.

The invention provides processes for selectively hydrolyzing one antipode of 2,3-o-substituted glycerol esters to give optically-active 2,3-o-substituted glycerol; the remaining esters also being optically-active. The chiral intermediates are useful in synthesizing chiral beta-adrenergic blocking agents for treatment of hypertension, heart disease, glaucoma, phospholipids, such as the platelet activating factor, and chiral mono-, di- and triglycerides.

BACKGROUND ART

Chiral glycerol derivatives such a 2R and 2S-glycerol 1,2-acetonides have been extensively used as building blocks for the synthesis of optically-active drugs [A. Tanaka and K. Yamashita, *Agri. Biol. Chem.*, 44 199 (1979); W. L. Nelson et al., *J. Org. Chem.*, 42, 1006 (1977); Y. Tsuda et al., *Chem. Pharm. Bull.*, 29, 3593 (1981)]. For example, 1 and 2 are key intermediates for the synthesis of chiral 3-aryloxy-1,2-propanediols such as R- and S-propranolol W. L. Nelson et al., *J. Org. Chem.*, 42, 1006 (1977)].

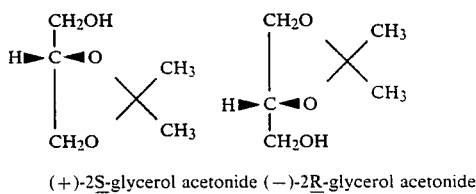

(+)-2S-glycerol acetonide    (−)-2R-glycerol acetonide 1                      2

While the (+)-2S-glycerol acetonide (1) is readily available from (2R,3S,4S,5R)-mannitol-1,2,5,6-diacetonide by the method of E. Baer, *Biochem. prep.*, 2, 31 (1952) (lead tetraacetate oxidation followed by catalytic reduction of the intermediates glyceraldehyde-2,3-acetonide), the (−)-2R-glycerol acetonide (2) is considerably more tedious to prepare and hence is less readily available. It has been prepared from the expensive, unnatural carbohydrates such as L-mannitol and L-arabinose [E. Baer and H. O. L. Fischer, *J. Am. Chem. Soc.*, 61, 761 (1939)] and, subsequently, was synthesized from L-galactono-1,4-lactone, [S. Morgenlie, *Carbohydrate Res.*, 107, 137 (1982)] although neither the isolated yield nor the optical purity of the product was described. More recently, 2 was prepared from tartaric acid [A. Tanaka et al., *Agric. Biol. Chem.*, 48, 2135 (1984); K. Fujita et al., *Tet. Lett.*, 23, 3507 (1982)] or from L-ascorbic acid [M. E. Jung and T. J. Shaw, *J. Am. Chem. Soc.*, 102, 6304 (1980)] using relatively long reaction sequences in moderate overall yield. Because of the serious disadvantages which characterize each of the aforementioned methods, the cost of 2 at the present time is high ($3,500/Kg, Pfanstiehl Laboratories, Waukegan, Ill.).

DISCLOSURE OF INVENTION

The process of this invention, which utilizes the hydrolytic processes of microorganisms, broadly comprises using microbial esterases to selectively cleave the ester grouping of one of the enantiomers of racemic esters of 2,2-dimethyl-1,3-dioxomolane-4-methenol (3) and 2,2-pentamethylene-1,3-dioxomolane-4-methanol (4).

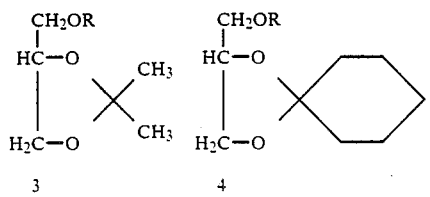

3                      4 where R is an acyl group having from 2 to about 4 carbon atoms.

The result is a kinetic resolution of the racemate.

The preferred substrate for the process of this invention comprises the esters of 4. It is to be understood, however, that the process is not to be considered as limited to the substrate compounds specifically set forth above but that R can represent any acyl group that can be hydrolyzed by the esteratic activity of microorganisms.

Broadly, microorganisms which can be used in the process of the present invention and which are capable of cleaving the ester molecules indicated above are those which produce hydrolytic enzymes. Microorganisms which are characterized by such esteratic activity are well known in the microbiological art but it has been found that those which have the particular characteristics necessary to the present process are rare. The microorganisms which are peculiarly suitable to the method of this invention are *Streptomyces parvulus* ATCC 19796 and *Micrococcus luteus* ATCC 9341.

In the process of the present invention the racemic ester substrate can be incorporated in a nutrient medium of standard composition in which such organisms are cultivated and the usual conditions of fermentation can then be employed to effect the hydrolytic transformation. Alternatively, the active hydrolytic principle can be removed from the growing culture of the microorganism, for example, by lysis of the cells to release the enzymes, or by suspension of the micelium in a fresh aqueous system. Also, if desired, the cells or the hydrolytic enzyme can be immobilized (M. D. Trevan, "Immobilized Enzymes," John Wiley & Sons, N.Y., 1980). So long as the active principle produced by the microorganisms is present in the medium any of these techniques can be used to selectively cleave the ester grouping without cleaving the ketal. The temperature, time and pressure conditions under which the contact of the glycerol ester derivative with the hydrolytic principle is carried out are interdependent as will be apparent to anyone skilled in the art. For example, with gentle heating and at atmospheric pressure the time required to effect the hydrolytic conversion will be less than if the process is carried out at room temperature, other conditions being the same. Of course, neither temperature, nor pressure, nor time, should be so high that the ester substrate is caused thereby to be degraded. More a growing culture of the microorganisms is being used, the process conditions should also be sufficiently gentle so the organism is not killed before it produces sufficient hydrolytic enzymes to effect the desired cleavage. Generally, the process can be carried out at a temperature in the range from about 10° C. to about 35° C., for from about 12 hours to about 10 days.

DETAILED DESCRIPTION OF THE INVENTION

The following examples are given by way of illustrating the present invention and are not to be considered as limiting the scope of the appended claims.

Synthesis of racemic acetyl ester of 2,2-pentamethylene-1,3dioxolane-4-methanol (6)

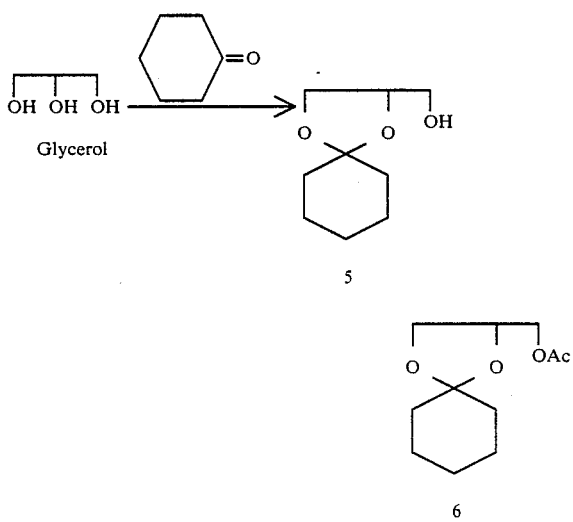

2,2-Pentamethylene-1,3-dioxolane-4-methanol (5): A mixture of 9.8 g (0.100 mol) cyclohexanone, 9.2 g (0.100 mol) glycerol, 0.48 g (0.25 mmol) p-toluenesulfonic acid and 90 ml of water started immediately. The reaction mixture was neutralized with 1 g (9.4 mmol) anhydrous sodium carbonate, stirred for 30 min at room temperature, filtered and concentrated, yielding 17.6 g crude hydroxy-ketal 5. $^1$H-NMR (CDCl$_3$, 90 MHz) 1.2–1.9 (m, (1OH), 5H$_2$C), 2.50 (s, 1H, HO), 3.42–4.40 (m, 5H, 2HC—O,HC—O).

Acetyl ester of 2,2-pentamethylene-1,3-dioxolane-4-methanol (6): The crude hydroxyketal 5, dissolved in 100 ml pyridine and 20 ml (0.21 mol) acetic acid anhydride, was stirred at 50° for 16 h. Extraction (250 ml, 2×250 ml Et$_2$O; 3×150 ml H$_2$O, 250 ml sat. brine solution), filtration and concentration of the organic phase, followed by a Kugelrohr-distillation (120°–130°, 2 Torr) gave 18.6 g (87%) acetate 6 as a colorless liquid. $^1$H-NMR (CDCl$_3$, 90 MHz) 1.2–1.8 (m, 1OH, 5H$_2$C), 2.08 (s, 3H, H$_3$C), 3.62–3.93, 3.97–4.5 (2 m, 5H, 2H$_2$C—O,H-C—O). $^{13}$C-NMR (CDCl$_3$, 25 MHz) 20.6, 24.0, 24.2, 25.4, 35.3, 36.7 (5CH$_2$, CH$_3$), 65.1, 66.5, 73.6 (3C—O), 110.5 (CO$_2$), 170.3 (COO).

The same procedure can be repeated for the synthesis of other substrates for use with the process of this invention by substituting the appropriate reagents in the above reaction sequence. Thus, instead of the cyclic ketone, cyclohexanone, in the above reaction, ketones derived from the paraffin hydrocarbons can be utilized, for example, acetone, to make compound 3. In addition esters other than the acetic ester can be readily obtained by utilizing the appropriate acid anhydride of the ester desired.

EXAMPLE 1

A. Fermentation. Surface growth from a one week old agar slant of *Streptomyces parvulus* ATCC 19796 on agar of the following composition:

|  | Gms |
|---|---|
| Yeast extract | 1 |
| Beef extract | 1 |
| Tryptose | 2 |
| FeSO$_4$ | 0.01 |
| Glucose | 10 |
| Agar | 20 |
| Distilled water, q.s. 1 liter, PH 7.2 | |
| (Sterilized 15 min at 20 p.s.i.) | |

The cells and spores in the agar slant were suspended in 1 ml of an 0.85% saline solution and were used to inoculate a 250 ml Erlenmeyer flask (F-1 stage) containing 50 ml of the following medium (Medium B):

|  | Gms |
|---|---|
| Glucose | 15 |
| Malt extract | 20 |
| Bacto peptone | 10 |
| Yeast extract | 5 |
| Distilled water, q.s. 1 liter, pH 6.8 | |
| (Sterilized for 15 min at 30 p.s.i.) | |

The flask was incubated at 25° C. on a rotary shaker (250 cycles/min-2" radius) for 48 hours, after which the contents were transferred to a 1 liter Erlenmeyer flask containing 250 ml of medium B for the propagation of the F-2 stage. After 24 hours of incubation under the conditions used in the growth of the F-1 stage, 500 mg of the (±) acetyl ester of 2,2-pentamethylene-1,3-dioxolane-4-methanol (6) was added to the flask. The F-2 stage flask was then incubated for an additional 48 hours under the conditions used for the F-1 stage.

B. Isolation. 48 hours after addition of the substrate, the F-2 stage was terminated by filtering the flask contents through a pad of celite and the filtrate was extracted with ethyl acetate (3×250 ml). The combined ethyl acetate extracts were dried over sodium sulfate and concentrated in vacuo to give a residue (430 mg). This residue was dissolved in 3 ml of a solvent mixture of Skelly B-ethyl acetate (5:1) and chromatographed over a silica gel (MN Kieselgel 60, Brinkmann) column (1.2×23 cm). Elution of the column with a solvent system comprised of Skelly B-ethyl acetate (5:1) afforded 190 mg of (−)-R-acetyl ester of 2,2-pentamethylene-1,3-dioxolane-4-methanol, [α]$_D^{25}$ −6.35° (c, 3.5 ether) (ee=0.98) and 192 mg of (+)-S-2,2-pentamethylene-1,3-dioxolane-4-methanol, which was converted into its acetyl derivative (acetic anhydride/pyridine), [α]$_D^{25}$ +4.73° (c, 3.7 ether) (ee=0.75).

C. The progress of the micrcbiological hydrolysis of 6 can be followed by gas-liquid chromatographic analyses using an OV101 column (90 cm). The temperature program began at 70° C. at an increment of 10° per min and terminated at 40° C. The retention time of the substrate, 6, was 5 min and that of the product, 5, was 6.3 min.

D. Determination of Optical Purity. The optical purity expressed in enantiomeric excess (ee) is determined by MR in the presence of the chiral lanthanide shift reagent, Eu(hfc)₃ (Aldrich). The molar ratio of the chiral shift reagent to the substrate was about 1.2–1.5.

EXAMPLE 2

Optically active (−)-R-acetyl ester of 2,2-dimethyl-1,3-dioxolane-4-methanol (ee=0.96) and (+)-S-2,2-dimethyl-1,3-dioxolane-4-methanol (ee=0.34) were prepared in accordance with the procedure of Example 1 except that (±)-acetyl ester of 2,2-dimethyl-1,3-dioxolane-4-methanol was used as the substrate.

EXAMPLE 3

Optically active (+)-S acetyl ester of 2,2-pentamethylene-1,3-dioxolane-4-methanol (ee=0.97) and (−)-R-2,2-pentamethylene-1,2-dioxolane-4-methanol (ee=0.32) were prepared in accordance with the procedure of Example 1 except that *Micrococcus luteus* ATCC 9341 was used as the microorganism to effect the stereoselective hydrolysis.

EXAMPLE 4

Optically active (+)-S-acetyl ester of 2,2-dimethyl-1,3-diaxolane- 4-methanol (200 mg) (ee=0.55) and (−)-R-2,2-dimethyl-1,3-dioxolane-4-methanol (220 mg) (ee=0.34) were prepared in accordance with the procedure of Example 1 except that *Micrococcus luteus* ATCC 9341 was used as the microorganisms to effect the transformation and (+)-acetyl ester of 2,2-dimethyl-1,3-dioxolane-4-methanol was used as the substrate.

I claim:

1. A method for resolving racemic 2,3-o-substituted glycerol esters which comprises exposing said esters to the fermentative action of enzymes produced by a microorganism selected from the group consisting of *Streptomyces parvulus* ATCC 19796 and *Micrococcus luteus* ATCC 9341 and recovering optically active 2,3-o-substituted glycerol and optically active 2,3-o-substituted glycerol esters.

2. The process of claim 1 wherein the exposure to the enzymes produced by the microorganism is accomplished curing cultivation of the microorganism in an aqueous nutrient medium under submerged aerobic conditions.

3. The process of claim 2 wherein the process is carried out at a temperature in the range from about 10°0 C. to about 35° C. for a period of from about 12 hours to about 10 days.

4. The process of claim 2 wherein the cells of the microorganism have been immobilized.

5. The process of claim 1 wherein the exposure to the enzymes produced by the microorganism is accomplished in a nutrient radium in which said enzymes have teen incorporated after they have been released from a growing culture of the microorganims and recovered.

6. The process of claim 5 wherein the enzymes have been immobilized.

7. The process of claim 1 wherein the microorganism is *Streptomyces parvulus* ATCC 19796.

8. The process of claim 1 wherein the microorganism is *Micrococcus luteus* ATCC 9341.

9. The process of claim 1 wherein the 2,3-o-substituted glycerol ester is selected from

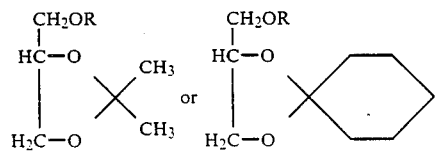

where R represents an acyl group having from 2 to about 4 carbon atoms.

10. The process of claim 9 wherein the 2,3-o-substituted glycerol ester is 2,2-dimethyl-1,3-dioxolane-4-methanol.

11. The process of claim 9 wherein the 2,3-o-substituted glycerol ester is 2,2-pentamethylene-1,3-dioxolane-4-methanol.

* * * * *